United States Patent [19]
Heller et al.

[11] Patent Number: 5,108,819
[45] Date of Patent: Apr. 28, 1992

[54] THIN FILM ELECTRICAL COMPONENT

[75] Inventors: James W. Heller, Englewood, Colo.; David Lipson; Kirk W. Johnson, Indianapolis, both of Ind.

[73] Assignee: Eli Lilly and Company, Indianapolis, Ind.

[21] Appl. No.: 479,897

[22] Filed: Feb. 14, 1990

[51] Int. Cl.$^5$ .............................................. B32B 3/00
[52] U.S. Cl. ...................................... 428/195; 428/40; 428/209; 428/423.5; 428/426; 428/433; 428/435; 428/457; 428/901; 501/66
[58] Field of Search ................ 428/901, 209, 40, 195, 428/426, 433, 423.5, 457, 542.8, 435; 501/66; 361/397, 398

[56] References Cited

PUBLICATIONS

Pyralin TM PD Processing Guidelines PI-2700, DuPont Electrics (1988).
"Thin Film Electrodes for an Artificial Ear", R. L. White et al., J. Vac. Sci. Technol. A 1(2), Apr.-Jun. 1983, pp. 287-295.
"Thin-Film Multielectrode Arrays for a Cochlear Prosthesis", Shamma-Donoghue et al., IEEE Transactions on Electron Devices, vol. Ed-29, No. 1, Jan. 1982, pp. 136-144.
"Fabrication of a Microbial Carbon Dioxide Sensor Using Semiconductor Fabrication Techniques", H. Suzuki et al., Electroanalysis, 1 (1989), pp. 305-309.
"Planar Amperometric Enzyme-Based Glucose Microelectrode", M. Koudelka et al., Sensors and Actuators, 18 (1989), pp. 157-165.
"Fabrication and Characterization of a Planar Electrochemical Cell and its Application as a Glucose Sensor", S. Gernet et al., Sensors and Actuators, 18 (1989), pp. 59-70.
"A Planar Glucose Enzyme Electrode", S. Gernet et al., Sensors and Actuators, 17 (1989), pp. 537-540.
"Fabrication of a Micro Oxygen Electrode and its Application", H. Suzuki et al., Proc.-Electrochem. Soc. 1987, 87-89 (Proc. Symp. Chem. Sens.), pp. 393-400 (Eng).

*Primary Examiner*—Patrick J. Ryan
*Assistant Examiner*—Elizabeth Evans
*Attorney, Agent, or Firm*—Douglas J. Taylor; Leroy Whitaker

[57] ABSTRACT

A biocompatible thin film electrical component is configured for use in a human body or other ionic liquid environment. A polyimide substrate is bonded to a glass carrier plate sized for handling by automatic equipment and a multiple-layer metal conductor is deposited on the substrate and patterned to define an electrical circuit or biosensor. The polyimide and the glass establish a bond therebetween that withstands handling yet is know using biocompatible releasing agents and techniques. The polyimide substrate and glass carrier plate preferably have similar thermal expansion properties to reduce the likelihood of fracture and delamination problems during release of the substrate from the carrier plate. An insulation layer covers the metal conductor and, in one embodiment, is made of polyimide having a cure temperature lower than the temperature at which interedifusion occurrs in the metal layers in the conductor.

19 Claims, 2 Drawing Sheets

THIN FILM ELECTRICAL COMPONENT

BACKGROUND AND SUMMARY OF THE INVENTION

The present invention relates to thin film electrical components, and particularly, to a flexible, microminiature, waterproof, biocompatible, thin film circuit package that can be patterned to function as a connector, sensor, or other electrical component. More particularly, the present invention relates to improvements in handling and configuring thin film circuit packages during manufacture.

A thin film is typically a film of 0.01 $\mu$m to 0.5 $\mu$m deposited on a glass, ceramic, or semiconductor substrate to form, for example, a capacitor, resistor, coil, or other circuit component. Thin film integrated circuits consist entirely of thin films deposited in a patterned relationship on a substrate.

One aim of the present invention is to develop an improved biocompatible thin film sensor or circuit suitable for use in the human body. It has been observed that satisfactory biocompatible thin film sensors or circuits cannot generally be produced by relying exclusively on the materials and techniques used to make conventional thin film structures.

Testing and monitoring of many biological conditions in the human body or other ionic liquid environments would be enhanced by the development of a waterproof thin film biosensor of miniature size and flexible character. However, conventional thin film structures are not generally designed to be biocompatible with the human body and are made using processes which are not suitable for use with biomaterials. Also, conventional thin film structures are not flexible.

A silicon wafer typically provides the foundation, platform, or carrier plate on which a conventional thin film structure is built. Automatic handling equipment is used to move the silicon wafer between manufacturing stations as a thin film structure is developed layer-by-layer on the silicon wafer. In this invention, the first thin film layer bonded to the silicon wafer carrier plate is used as a substrate of the thin film structure. Once the thin film structure is constructed, the silicon wafer carrier plate is released from attachment to the substrate of the thin film structure and discarded.

A thin film structure can be damaged during the release of the thin film structure from its silicon wafer carrier plate if the structure is made of any material which is incompatible with the acid etching solution or other release agent used to break the bonds coupling the substrate of the thin film structure to its silicon wafer carrier plate. It has been observed that many biomaterials of the type that could be used in the construction of a biologically compatible thin film structure are damaged or lose function upon exposure to conventional silicon wafer-releasing agents. The etching solutions normally used to dissolve a silicon wafer carrier plate are not compatible with biomaterials contained in a biocompatible thin film structure.

It has also been observed that thin film metal conductors deposited on a polymer substrate coupled to a carrier plate tend to fracture and delaminate upon release of the polymer substrate from its carrier plate foundation. It is thought that any difference in the coefficients of thermal expansion of the polymer substrate and its carrier plate foundation leads to the development of internal stresses in the polymer substrate as it is heat-cured, because its coefficient of thermal expansion is different from the carrier plate. Thin film structure fracture and delamination problems can result unless careful attention is given to the thermal expansion coefficients of the carrier plate foundation and substrate materials used to construct the thin film structure.

Conventional thin film structures are known to contain an adhesion metal film to enhance bonding of a noble metal film to its underlying polymer substrate. Such an adhesion metal film layer is a useful bonding tool because noble metals used to form electrical circuits in thin film structures do not adhere well directly to polymer substrates. For that reason, the adhesion metal layer is situated between the polymer substrate and the noble metal film layer.

It has been observed that thin film structures suffer performance losses because of interdiffusion of abutting adjacent adhesion and noble metal film layers during any high-temperature processing of the thin film structure, for example, during heat-curing of a polymer precursor solution to provide a polymer insulation layer on the metal film layers. Performance losses include, for example, loss of flexibility of the thin film structure itself and development of metal film layer adhesion problems. In addition to these mechanical problems, metal interdiffusion can cause changes to occur in the electrical properties of the noble metal layer.

The common solution to the metal interdiffusion problem in the semiconductor industry is the addition of a refractory metal layer (e.g., tungsten or tantalum) between the adhesion and noble metal film layers. This extra layer acts as an interdiffusion barrier. Processing of a thin film structure, however, is severely complicated by the deposition and patterning of such an additional refractory metal film layer.

One object of the present invention is to provide a biologically compatible thin film electrical component suitable for use in the human body or any other ionic liquid environment.

Another object of the present invention is to provide a thin film electrical component configured and patterned to function as a biosensor includable in a medical device implanted in a human body and a method of making this thin film electrical component to preserve its biosensor function capability.

Still another object of the present invention is to provide a thin film structure which can be fabricated without the occurrence of stress damage at the release of the thin film structure substrate from its carrier plate foundation.

Yet another object of the present invention is to provide a thin film structure that can be insulated without interdiffusion of metal film layers contained in the thin film structure.

According to the present invention, a thin film electrical component includes a rigid glass carrier plate, a substrate bonded to the rigid glass carrier plate, and means for providing an electrical circuit. The substrate comprises a polymer establishing a bond with the rigid glass carrier plate that is broken upon immersion of the substrate and the rigid glass carrier plate in either a boiling water bath or a room temperature physiologic saline bath to release the substrate from attachment to the rigid glass carrier plate. The means for providing an electrical circuit is bonded to the substrate and undisrupted during release of the substrate attachment to the rigid glass carrier plate.

One feature of the present invention is the provision of a thin film electrical component in which the polymer substrate can be released from its carrier plate without the use of any release agent or technique that could damage biomaterials contained in the substrate or means for providing an electrical circuit formed on the substrate. The selection of the proper glass for the carrier plate and the proper polymer for the substrate is critical. In particular, a polymer that develops a bond to glass that is strong enough only to withstand circuit fabrication processes but may be broken with biocompatilbe boiling water or biocompatible warm saline exposure is an important feature of the invention. Advantageously, the use of non-biocompatible silicon-etching release agents is avoided.

Those skilled in the art will recognize that an unmodified PMDA-ODA type polyimide is generally considered to be inferior compared to other possible substrate materials because of its marginal adhesive strength when bonded to most carrier plate foundations. Thus, for most thin film applications, adhesion-promoting agents are added to it so that this polyimide is modified to improve its bonding capability. Nevertheless, in the present invention, marginal adhesive strength is desirable to permit the glass carrier plate to be released from the polyimide substrate using biocompatible releasing agents and techniques. Thus, in the preferred embodiment, the polymer substrate comprises an unmodified PMDA-ODA type polyimide.

In preferred embodiments, the rigid glass carrier plate comprises a low-expansion type glass having a characteristic coefficient of thermal expansion and the polymer forming the substrate comprises a polyimide having a coefficient of thermal expansion that is substantially equivalent to the coefficient of thermal expansion of the low-expansion glass. Such a match in thermal expansion coefficients will cause the rigid glass carrier plate and the polymer substrate carrying the means for providing an electrical circuit to expand at about the same rate during exposure of the thin film structure to an elevated temperature. Advantageously, separation of the means for providing an electrical circuit from the substrate is avoided during release of the polymer substrate from attachment to the rigid glass carrier plate.

Accordingly, another feature of the present invention is that the carrier plate glass and the substrate polymer are carefully selected so that their coefficients of thermal expansion are about the same. Advantageously, thermal matching of this type reduces the likelihood that serious fracture and delamination problems will arise during release of the polymer substrate from the glass carrier plate.

Yet another feature of the present invention is the provision of a polymer insulation layer with a relatively low cure temperature. Without metal interdiffusion considerations, a logical choice for this insulation layer might be a photoimageable polyimide because the layer can be patterned without the use of additional photoresist steps. Unfortunately, currently available photoimageable polyimides require a high-cure temperature (450° C.) to drive out the photosensitizers. In the preferred embodiment, a BTDA-ODA polyimide is used, with positive photoresist, to form the patterned insulation coating. This material can be cured as low as 250° C., causing significantly less interdiffusion and resulting problems.

In the preferred embodiment, one type of polyimide is used to provide the polymer substrate and a different type of polyimide is used to provide the polymer insulator. The selection of the "substrate" polyimide is governed by its releasability and thermal-expansion compatibility with a glass carrier plate. For example, either a PMDA-ODA or BPDA-PPD type polyimide is suitable. On the other hand, the selection of the "insulator" polyimide is governed by the magnitude of its cure temperature compared to the minimum temperature at which metals in the thin film electrical component begin to interdiffuse and by its adhesive strength to the underlying polymer and metal layer. For example, as noted above, a BTDA-ODA polyimide is suitable.

Also according to the present invention, a method is provided of making a thin film electrical component. The method comprises the steps of providing a rigid glass carrier plate having a flat surface, coating the flat surface with a first polyamic acid precursor solution, and curing the first polyamic acid precursor solution using heat at a first temperature to provide a layer of polyimide film bonded to the flat surface. In a preferred embodiment of the present invention, the polyimide film has a coefficient of thermal expansion that is substantially equivalent to the coefficient of thermal expansion of the rigid glass carrier plate so that creation of internal stresses in the polyimide film during curing is avoided. In certain other embodiments, glass carrier plates and polyimide films having substantially different coefficients of thermal expansion can be used.

Preferably, the coating step further comprises the steps of dispensing the first polyamic acid precursor solution onto the flat surface of the rigid glass carrier plate, and spinning the rigid glass carrier plate about an axis orthogonal to the flat surface to create a smooth polyamic acid precursor solution coating of substantially uniform thickness across the flat surface. This is a conventional spin-coating process commonly used in the semiconductor industry. The rigid glass carrier plate is spun at a speed between 1,000 and 6,000 revolutions per minute during the spinning step.

The method further includes the steps of forming means for providing an electrical circuit on the polyimide film, and exposing the rigid glass carrier plate, the polyimide film, and the means for providing an electrical circuit to either a hot water bath or a body temperature physiologic saline bath for a period of time sufficient to break the bond connecting the polyimide film to the rigid glass carrier plate. The warm saline bath provides a biocompatible releasing agent which operates to cause the polyimide film to be released from the rigid glass carrier plate without separating the means for providing an electrical circuit from the polyimide film.

An electrical circuit is provided in the thin film electrical component by depositing a first adhesive metal layer on the polyimide film, a noble metal layer on the first adhesive metal layer, and a second adhesive metal layer on the noble metal layer to sandwich the noble metal layer between the first and second adhesive metal layers, and patterning the deposited noble metal layer and first and second adhesive metal layers to define means on the polyimide film for providing an electrical circuit. Next, a second polyamic acid precursor solution is provided on the means for providing an electrical circuit by dispensing the second polyamic acid precursor solution onto the means for providing an electrical circuit, and spinning an assembly comprising the rigid glass carrier plate, the polyimide film, the means for providing an electrical circuit about an axis orthogonal to the flat surface of the rigid glass carrier plate. The assembly is spun to create a coating of second polyamic acid precursor solution on predetermined exposed portions of the polyimide film and the means for providing an electrical circuit.

The second polyamic acid precursor solution is then cured using heat at a second temperature to provide a polyimide insulation coating on the means for providing an electrical circuit. In cases where interdiffusion between noble and adhesive metal layers is a problem, the second temperature is less than a characteristic minimum temperature at which interdiffusion of the noble metal layer and the first and second adhesive metal layers occurs so that substantial interdiffusion of the noble metal layer and the first and second adhesive metal layers is avoided during heat curing of the second polyamic acid precursor solution.

Additional objects, features, and advantages of the invention will become apparent to those skilled in the art upon consideration of the following detailed description of a preferred embodiment exemplifying the best mode of carrying out the invention as presently perceived.

BRIEF DESCRIPTION OF THE DRAWINGS

The detailed description particularly refers to the accompanying figures in which.

DETAILED DESCRIPTION OF THE DRAWINGS

Figure 1:
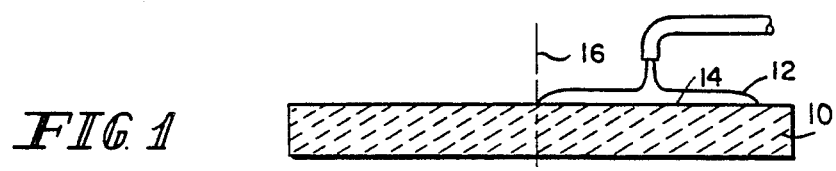
FIG. 1 is a diagrammatic sectional view of a glass carrier plate during deposition of a polymer precursor solution onto a flat surface of the glass carrier plate.
Figure 7:
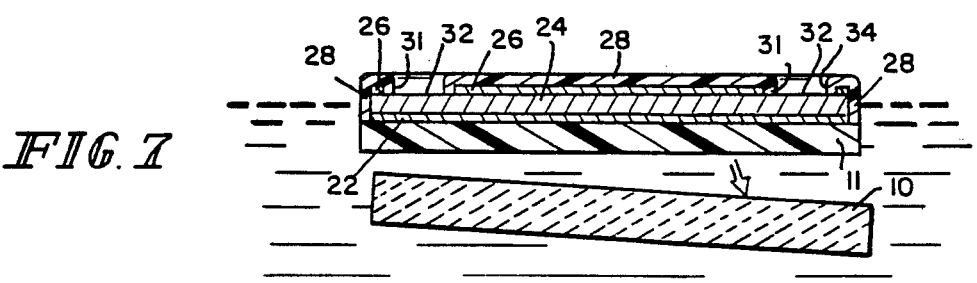
FIG. 7 is a diagrammatic sectional view of the component of FIGS. 5 and 6 immersed in a liquid bath to release the glass carrier plate from attachment to the polymer substrate.

A process for making a thin film electrical component is illustrated in FIGS. 1–7. The finished component is illustrated in FIG. 7. As shown in FIG. 1, a clean glass plate 10 is used at the beginning of the manufacturing process to provide a rigid carrier plate or foundation for the thin film electrical component. A "photomask" blank is preferred because of its precise flatness and smoothness and thermal stability. In the preferred embodiment, the plate 10 is a low-expansion glass consisting essentially of 60% $SiO_2$, 18% RO, 15% $Al_2O_3$, 5% $B_2O_3$, 1% $Na_2O$, and 1% $K_2O$. It will be understood that RO stands for "unknown metal oxide impurities."

Square or circular glass plates may be used to provide plate 10 with outside dimensions ranging from 3 inches (7.62 cm) to 6 inches (15.24 cm) and thicknesses of about of 0.030 inches (0.076 cm) to 0.090 inches (0.228 cm). A standard "silicon wafer or photomask" size can be selected for plate 10 to accommodate automatic handling and processing equipment. Glass plate 10 can be cleaned using a conventional cleaning solution prior to use and may be reused indefinitely.

Figure 2:
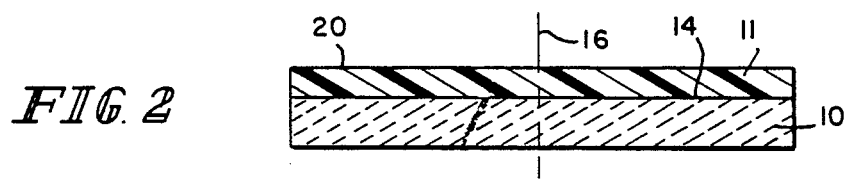
FIG. 2 is a diagrammatic elevation view of a polymer substrate on the glass carrier plate of FIG. 1.

Referring to FIGS. 1 and 2, a polymer substrate 11 is formed by spin-coating liquid polyamic acid 12 onto a top flat surface 14 of the rigid quartz-glass plate 10 as the plate 10 is spun about an axis 16 that is orthogonal to the flat surface 14. Illustratively, the glass carrier plate 10 is spun at a speed between 1,000 and 6,000 revolutions per minute. This spin-coating technique is desirable because it results in a smooth and uniform coating.

The polyamic acid precursor solution 12 on glass plate 10 is imidized using a two-stage heat cure process to provide a polymer substrate 11 comprising a flat, uniform sheet of polyimide. Substrate 11 is made of a polymer that has desirable electrical properties, a surface that metal can be deposited onto, and desirable release properties. PMDA-ODA (pyro-mellitic dianhydride oxydianaline) type polyimide without adhesion-promotion additives is the preferred polymer. This material bonds very weakly to glass and such bonds may be broken with boiling water or warm saline exposure. However, the bond between the polyimide and the glass is sufficient to withstand thin film circuit fabrication processes. For example, the bonding of this type of polyimide to glass is sufficient to withstand typical photolithographic processes such as baking, acid etching, photoresist developing, and sputtering. Further, the coefficient of thermal expansion of the polyimide is about the same as the coefficient of thermal expansion of the preferred glass plate 10 so that fracture and delamination problems will not adversely affect the thin film electrical component upon release of the polyimide substrate 11 from the glass carrier plate 10.

The thickness of polymer substrate 11 can be in the range of 10 to 100 $\mu m$. This is controlled by the viscosity of the polyamic acid precursor solution 12 and the spin speed of the glass carrier plate 10. Thick coatings (greater than approximately 25 $\mu m$) of polyimide are achieved by multiple coat-cure cycles. In another embodiment, a pre-made KAPTON® sheet is used to provide polymer substrate 11 instead of a spin-coated liquid polyamic acid 12 subjected to a two-stage heat cure process.

Figure 3:
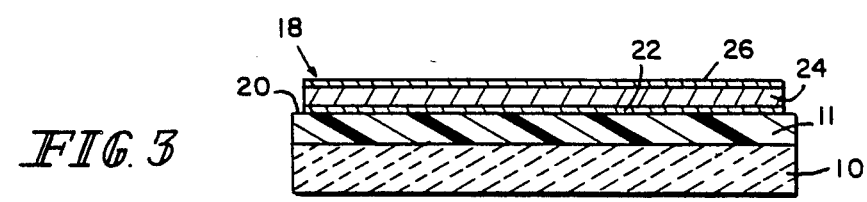
FIG. 3 is a diagrammatic view of a metal composite conductor consisting of three metal layers on the polymer substrate of FIG. 2.
Figure 4:
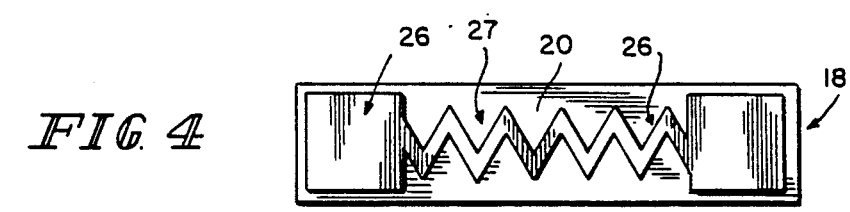
FIG. 4 is a top plan view of the component of FIG. 3 showing configuration of the multiple-layer metal conductor to provide a circuit element.

The metal layers are deposited and patterned as shown in FIGS. 3 and 4. A flexible conductor 18 is formed on the top surface 20 of polymer substrate 11 and includes a first adhesive metal layer 22 bonded to top surface 20, a noble metal layer 24 bonded to first adhesive metal layer 22, and a second adhesive metal layer 26 bonded to the noble metal layer 24 to trap the noble metal layer 24 between the first and second adhesive metal layers 22, 26.

The three metal layers 22, 24, and 26 are deposited successively using standard thin film vacuum deposition methods. D.C. magnetron sputtering is the preferred method because of its relatively high deposition rate and ability to form highly adhesive films. Gold is the preferred noble metal because of its high ductility, although platinum and palladium are suitable alternatives.

Chromium is the preferred adhesive metal, although titanium, tungsten, and tantalum are suitable alternatives. The adhesive metal layers are about 0.01 μm to 0.02 μm thick and the noble metal layer is about 0.1 μm to 0.2 μm thick. It will be appreciated that it is not necessary to include a refractory metal layer at the interface between each adhesive and noble metal layer because of the selection of a polymer insulator coating having a low heat-cure temperature as described below.

To provide an electrical component on the substrate 10, the metal layers 22, 24, and 26 can be patterned using a variety of standard photolithography processes (not shown). A representative circuit pattern 27 (e.g., a resistor) is shown in FIG. 4. It will be appreciated that circuit pattern 27 could be any electrical element, integrated circuit, sensor, or other component depending upon the intended function of the thin film structure.

A suitable photolithography process generally involves the application of a photoresist or masking material by spin coating. This material is baked until dry. The material is then exposed to ultraviolet light through a mask which contains the circuitry patterns. The photoresist is developed, leaving only selected areas masked. Exposed metal may be removed by wet chemical or dry plasma etch. The photoresist can then be stripped by solvent dip or plasma etching. In a preferred embodiment, positive photoresist, wet etching, and solvent stripping is used. Line widths and spaces as small as 5 μm have been made and dimensions as small as 1 μm are possible.

Figure 5:
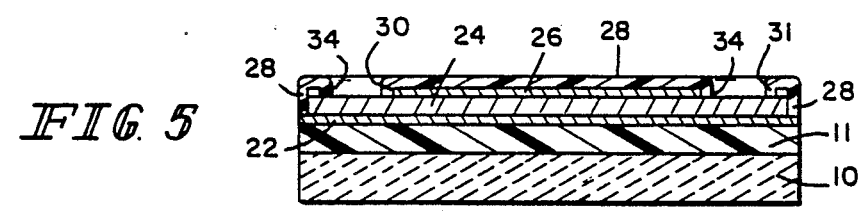
FIG. 5 is a diagrammatic sectional view of the component of FIG. 4 showing an access opening formed in the top metal layer and an insulation coating covering portions of the metal conductor.
Figure 6:
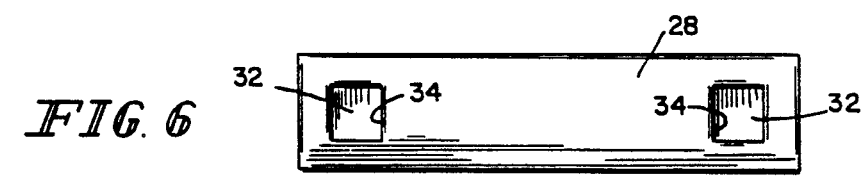
FIG. 6 is a top plan view of the component of FIG. 5 showing a pair of uninsulated lead-attachment sites.

An insulator cover 28 is needed to insulate the conductor 20 electrically and prevent exposure of the potentially corrosive adhesive metal to liquids. The same patterning process that was used to define the electrical circuit 27 in conductor 20 is now usable to remove the top adhesive metal layer 26 in areas of the conductor 20 that will be uninsulated. As shown in FIG. 5, the second adhesive metal layer 26 is formed to include a pair of access openings 30 therein to expose a portion of the underlying noble metal layer 24 to provide a lead-attachment site 32 on the noble metal layer 24. The metal in layer 26 is removed about 5-10 μm beyond the intended location of the insulation opening edge 34. This distance must be sufficient to ensure coverage of adhesive metal edge 30 but minimal so that most of the insulation layer 28 is in contact with the adhesive metal. Polyimide substrate and insulation layers 11, 28 do not adhere well to the noble metal 24 directly. It is this precise alignment step that makes the use of spun-on substrates preferable in the present invention. It is difficult to hold free-standing films sufficiently flat to ensure alignment accuracies of 5 to 10 microns across a 3 inch (7.62 cm) to 6 inch (15.24 cm) sheet. As shown in FIG. 5, the polyimide coating defining insulator cover 28 includes a wall 31 that extends into the access opening 30 formed in the second adhesive metal layer 26 to contact the noble metal layer 22.

The insulation layer 28 is deposited and patterned. In one preferred embodiment, the insulation layer 28 is comprised of a BTDA-ODA type polyimide which can be cured at a temperature as low as 250° C. to minimize the opportunity for metal interdiffusion problems in conductor 20 to develop. Coating thicknesses of 1-25 μm can be used to provide insulation layer 28. Alternatively, a PMDA-ODA type polyimide can be used to provide insulation layer 28. Photoimageable polyimides are preferred because non-photoimageable polyimides require more processing steps.

The insulation layer 28 is fabricated by spin-coating a polyamic acid precursor solution on conductor 20 as mounted on polymer substrate 11, curing the precursor solution to form the chosen polyimide at a temperature that is less than the minimum temperature at which interdiffusion of the noble metal layer 24 and the adhesive metal layers 22, 26 occurs, applying photoresist, etching, and stripping. Advantageously, substantial interdiffusion of the noble metal layer 24 and adhesive metal layers is avoided by curing the polyamic acid precursor solution-forming insulator cover 28 at a low temperature. It will be appreciated that the cure temperature of the polymer precursor used to form the polymer substrate 11 is not limited to this low temperature because it is heat-cured before any of the metal layers 22, 24, and 26 are deposited thereon.

It has been discovered during work on the present invention that if gold and chromium are employed as the noble and adhesion metals, respectively, interdiffusion (which leads to sensor cracking) between the noble and adhesion metal layers does not occur even when a polyimide having a high cure temperature is used to provide insulation layer 28. If a gold/chromium metal combination is used, high and low temperature polyimides can be used to provide insulation layer 28. It has been observed that a metal layer interdiffusion problem exists if any of the other noble or adhesion metals listed above are substituted for gold or chromium, e.g., platinum for gold or titanium for chromium. Accordingly, the gold/chromium combination is the best mode at present.

Figure 8:
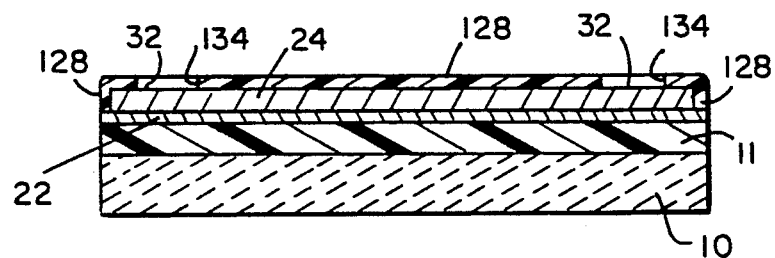
FIG. 8 is a diagrammatic sectional view of a component in accordance with another embodiment of the invention.
Figure 9:
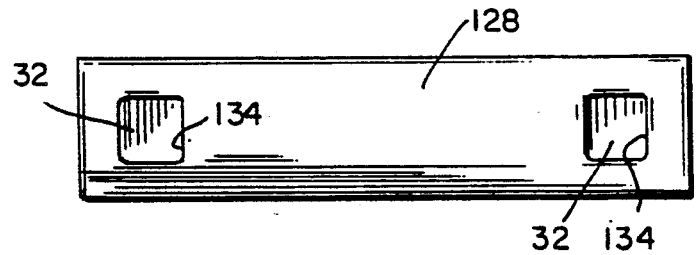
FIG. 9 is a top plan view of the component of FIG. 8 showing a pair of uninsulated lead-attachment sites.

In another embodiment of the present invention illustrated in FIGS. 8 and 9, these elements referenced by numbers identical to those in FIGS. 1-7 perform the same or similar function. The primary features distinguishing this embodiment from the previous embodiment is the use of a room temperature vulcanizing polymer to form the insulation layer and the absence of an adhesive metal layer between the noble metal layer and the insulation layer.

A conformal coating is used to form insulation layer 128 as shown in FIGS. 8 and 9. In a preferred embodiment, this coating is a synthetic polymer elastomer consisting essentially of a silicone resin such as dimethyl siloxane and an adhesion promoter such as methoxy silane. A suitable coating material is MS-460 TM resin available from Miller-Stephenson Chemical Company, Inc. of Danbury, Conn. This resin is available in solution for spin-on application or aerosol for spray-on application. Use of the spray-on technique is preferred because it is more amenable to mass production.

The silicone resin used to provide insulation layer 128 is a one-part system that cures in place at room temperature. It is an alternative to heat-cure polymers of the type curable only at the high temperatures that can cause metal interdiffusion problems. As noted above, there are some thin film applications where the metal conductors cannot be exposed to the high temperatures required to cure the polymer insulation layer film.

Another advantage of conformal coating materials, particularly silicone resins, is that they are more hydrophobic than other materials such as polyimides. The hydrophobic nature of conformal coatings, particularly the silicones, results in a lower amount of moisture pickup. Also, the preferred conformal coating adheres well to gold, which eliminates the need for a layer of adhesive metal between the noble metal layer 24 and the insulation layer 128. This decreases the number of processing steps required for fabrication of the thin film electrical component and, in turn, decreases the cost of producing the component.

Access openings 134 are easily formed in the insulation layer 128 after it cures. These openings can be created, for example, using either a dry plasma etch or by masking these areas prior to application of the conformal coating to the noble metal layer 24. The conformal coating 128 is a flexible material well-suited for use in a thin film electrical component that must be able to be flexed in use.

The final step is to release the polymer substrate 11 from the rigid glass carrier plate 10 as shown in FIG. 7. Two methods are suitable: 3 hour immersion in a 100° C. water bath or 24-hour immersion in a 37° C. physiologic saline bath. These times and temperatures may be varied slightly while still achieving the same result. The boiling water method is the most expeditious process for production. The body temperature saline process is useful where temperature sensitive materials such as enzymes, antibodies, or other biomaterials have been attached to the circuitry.

An additional step can be added before the substrate 11 is released from glass carrier plate 10. The outline of the thin film electrical component may be cut out with high accuracy using an excimer laser. The ultraviolet wavelength of this laser cuts polyimide rapidly but does not damage glass used to provide the carrier plate 10. In addition, this cutting mechanism generates no mechanical or thermal disruption which could damage biomaterials.

Very thin, flexible substrates are required for biosensors. A biosensor must be small enough to fit into a hypodermic needle or a venous or arterial catheter and withstand some flexing. This type of substrate is not easily handled or held flat, two necessities for cost-effective photolithographic production. Biosensor substrates must also be free of contaminants and be biocompatible. All of these requirements are met by a thin film electrical component in accordance with the present invention. High purity liquid polymer precursors are available and relatively inert biologically when cured. Glass plates are available with very good flatness and can be loaded into various cassette mechanisms for automatic handling and transfers. Also, a means is provided for releasing the thin film structure without damage to biomaterials.

Flexibility is a main advantage of the circuitry used to construct the thin film electrical component of the present invention. Curved and three-dimensional thin film structures can be built as a result of the flexible character of the conductor 20. The flexibility of the thin film electrical component makes it easily adaptable to provide a sensor compliable with a surface to be measured or a connector. By contrast, typical thin film or semiconductor substrates such as silicon, alumina, and silicon dioxide are very brittle in such thin sections.

The small conductor and insulator feature size results in very small overall device size. This is particularly advantageous for portable or implanted devices. It is also useful for high-density connectors such as those that interface directly with integrated circuitry. There is at least a ten-fold reduction in size compared to standard flex circuitry.

The waterproof nature of this circuit gives it the advantage of being able to operate in many adverse environments not suitable for traditional circuitry. These include: fresh water, salt water, physiologic saline (body fluid), boiling water, and steam. This opens many medical, industrial, and marine applications.

Polyimide is relative inexpensive compared to silicon and other typical microcircuit foundation materials. This means that one can afford to make the connecting leads on the same substrate as the active circuitry, thereby eliminating wire bonds and connectors. Polyimide has been shown to be biologically inert. Liquid polyamic acid is available in higher purity levels than sheet polyimide.

Many electrical components can be made simply by patterning the metal and insulation layers 22, 24, 26, and 28. These include resistors, capacitors, connectors, antennae, contact pads, electrodes, heaters, inductors, fuses, and thermistors.

In addition, piezoelectric, photoresistive, or magnetic films may be applied yielding sensing elements for force, light, and magnetic fields. The noble metal surface 24 can be electroplated to form electrochemically useful detection electrodes (i.e., platinum, silver/silverchloride). Active devices (optoelectronic components, transistors, integrated circuits) may be attached to the circuit to achieve amplification, regulation, or other functions.

An area of wide application is implanted medical devices. These could be electrochemical sensors, electrodes, or other physical sensors for strain, temperature, or fluid conductivity. Stimulating electrodes for the cochlea, heart, brain, or spinal column could also be made. The geometries allow such devices to be built to fit inside small size catheters and hypodermic needles.

Although the invention has been described in detail with reference to certain preferred embodiments, variations, and modifications exist within the scope and spirit of the invention as described and defined in the following claims.

What is claimed is:

1. A thin film electrical component comprising
   a rigid glass carrier plate,
   a substrate bonded to the rigid glass carrier plate, the substrate comprising a polymer establishing a bond with the rigid glass carrier plate that is broken upon immersion of the substrate and the rigid glass carrier plate in one of a hot water bath and a warm temperature physiologic saline bath to release the polymer from attachment to the rigid glass carrier plate, and
   means for providing an electrical circuit, the providing means being bonded to the substrate and undisrupted during release of the substrate from attachment to the rigid glass carrier plate.

2. The component of claim 1, wherein the rigid glass carrier plate comprises a low-expansion glass having a characteristic coefficient of thermal expansion and the polymer comprises a polyimide having a coefficient of thermal expansion that is substantially equivalent to the coefficient of thermal expansion of the low-expansion glass so that the rigid glass carrier plate and the substrate carrying the means for providing an electrical circuit will expand at about the same rate during exposure to an elevated thermal-expansion temperature sufficient to break the bond between the substrate and the rigid glass carrier plate, thereby avoiding separation of the means for providing an electrical circuit from the substrate during release of the substrate from attachment to the rigid glass carrier plate.

3. The component of claim 2, wherein the polyimide is one of a PMDA-ODA type polyimide and a BPDA- PPD type polyimide, and the low-expansion glass consists essentially of 60% $SiO_2$, 18% RO, 15% $Al_2O_3$, 5% $B_2O_3$, 1% $Na_2O$, and 1% $K_2O$.

4. The component of claim 1, wherein the means for providing an electrical circuit comprises an adhesive metal layer bonded to the substrate and a noble metal layer bonded to the adhesive metal layer, and further comprising insulating means on the substrate for providing an insulating cover on the means for providing an electrical circuit, the insulating means comprising a polyamic acid precursor solution cured at a heat-cure temperature to provide a polyimide coating, the polyamic acid precursor solution having a heat-cure temperature that is less than a characteristic minimum temperature at which interdiffusion of the noble metal layer and the adhesive metal layer occurs so that substantial interdiffusion of the noble metal layer and the adhesive metal layer is avoided during heat curing of the polyamic acid precursor solution.

5. The component of claim 4, wherein the adhesive metal layer is a material selected from the group consisting essentially of titanium and chromium, the noble metal layer is a material selected from the group consisting essentially of gold, platinum, and palladium, and the polyimide coating resulting from heat curing the polyamic acid precursor solution is one of a PMDA-ODA type polyimide and a BTDA-ODA type polyimide.

6. The component of claim 4, wherein the means for providing an electrical circuit further comprises another adhesive metal layer bonded to the noble metal layer to lie between the noble metal layer and the insulating means.

7. The component of claim 6, wherein said another adhesive metal layer is formed to include at least one access opening therein to expose a portion of the underlying noble metal layer to provide a lead-attachment site on the noble metal layer.

8. The component of claim 7, wherein the polyimide coating extends into the access opening formed in said another adhesive metal layer to contact the noble metal layer.

9. A thin film electrical component comprising
a polymer substrate,
a first adhesive metal layer bonded to the polymer substrate,
a noble metal layer bonded to the first adhesive metal layer,
a second adhesive metal layer bonded to the noble metal layer, the noble metal layer being sandwiched between the first and second adhesive metal layers, and
a polymer insulator bonded at least to the first and second adhesive metal layers to cover all exposed surfaces of the first and second adhesive metal layers unbonded to one of the polymer substrate and the noble metal layer.

10. The component of claim 9, wherein the second adhesive metal layer is formed to include at least one access opening therein to expose a portion of the underlying noble metal layer to provide a lead-attachment site on the noble metal layer 11. The component of claim 10, wherein the polymer insulator includes a wall extending through each access opening formed in the second adhesive metal layer to contact the noble metal layer.

12. The component of claim 9, wherein the polymer insulator comprises a polyamic acid precursor solution cured at a heat-cure temperature to provide a polyimide coating, the polyamic acid precursor solution having a heat-cure temperature that is less than a characteristic minimum temperature at which interdiffusion of the noble metal layer and the first and second adhesive metal layers occurs so that substantial interdiffusion of the noble metal layer and the first and second adhesive metal layers is avoided during heat curing of the polyamic acid precursor solution.

13. The component of claim 12, wherein each of the first and second adhesive metal layers is a material selected from the group consisting essentially of titanium and chromium, the noble metal layer is a material selected from the group consisting essentially of gold, platinum, and palladium, and the polyimide coating resulting from heat curing the polyamic acid precursor solution is one of a PMDA-ODA type polyimide and a BTDA-ODA type polyimide.

14. The component of claim 12, wherein the polyamic acid precursor solution is applied directly to at least said exposed surfaces of the first and second adhesive metal layers to create the polymer insulator without providing a separate diffusion barrier layer of material between the polymer insulator and said exposed surfaces.

15. The component of claim 9, further comprising a rigid glass carrier plate, the polymer substrate being bonded to the rigid glass carrier plate to facilitate handling of the polymer substrate by automatic equipment.

16. The component of claim 15, wherein the polymer substrate comprises a PMDA-ODA type polyimide establishing a bond with the rigid glass carrier plate that is broken upon immersion of the polymer substrate and rigid glass carrier plate in one of a hot water bath and a warm temperature physiologic saline bath to release the polymer substrate from attachment to the rigid glass carrier plate without damaging any of the metal layers, the polymer insulator, and the bonds therebetween.

17. The component of claim 15, wherein the rigid glass carrier plate comprises a low-expansion glass having a characteristic coefficient of thermal expansion and the polymer substrate comprises a polyimide having a coefficient of thermal expansion that is substantially equivalent to the coefficient of thermal expansion of the low-expansion glass so that the rigid glass carrier plate and the polymer substrate attached thereto will expand at about the same rate during exposure of said plate and substrate to elevated thermal-expansion temperature sufficient to break the bond between said plate and substrate, thereby avoiding fracture of the metal layers on said polymer substrate during release of the polymer substrate from attachment to the rigid glass carrier plate.

18. The component of claim 17, wherein the polyimide is one of a PMDA-ODA type polyimide and a BPDA-PPD type polyimide, and the low-expansion glass consisting essentially of 60% $SiO_2$, 18% RO, 15% $Al_2O_3$, 5% $B_2O_3$, 1% $Na_2O$, and 1% $K_2O$.

19. An apparatus for preparing a thin film electrical component comprising
a rigid glass carrier plate, and
a substrate bonded to the rigid glass carrier plate, the substrate comprising a polymer establishing a bond with the rigid glass carrier plate that is broken upon immersion of the substrate and the rigid glass carrier plate in one of a hot water bath and a warm temperature physiologic saline bath to release the polymer from attachment to the rigid glass carrier plate.

* * * * *